United States Patent
Majumder et al.

(10) Patent No.: US 9,174,891 B2
(45) Date of Patent: Nov. 3, 2015

(54) DETERGENT ALKYLATION PROCESS FOR CONTROLLING ALKYLATION EXOTHERM WITH PARAFFINS

(71) Applicant: UOP LLC, Des Plaines, IL (US)

(72) Inventors: Debarshi Majumder, Forest Park, IL (US); Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 103 days.

(21) Appl. No.: 13/922,533

(22) Filed: Jun. 20, 2013

(65) Prior Publication Data

US 2014/0378722 A1  Dec. 25, 2014

(51) Int. Cl.
*C07C 2/66* (2006.01)
*C07C 6/12* (2006.01)
*C07C 2/64* (2006.01)

(52) U.S. Cl.
CPC .... *C07C 2/64* (2013.01); *C07C 2/66* (2013.01)

(58) Field of Classification Search
USPC .................................................. 585/445, 449
See application file for complete search history.

(56) References Cited

U.S. PATENT DOCUMENTS

| 7,655,824 | B2 | 2/2010 | Riley | |
|---|---|---|---|---|
| 7,973,206 | B1 | 7/2011 | Riley | |
| 8,058,199 | B2 | 11/2011 | Riley | |
| 8,158,839 | B2 | 4/2012 | Riley | |
| 2008/0194895 | A1* | 8/2008 | Sohn et al. | 585/435 |

* cited by examiner

*Primary Examiner* — Thuan D Dang

(57) ABSTRACT

The process of producing an alkylbenzene compound from the alkylation of an aromatic compound with an acyclic monoolefin is an exothermic process. A process for maintaining a relatively constant temperature improves the process and allows for controlling the yields. The process includes recycling a compound through the reactor that is relatively inert, but will moderate the exotherm, while maintaining the 2-phenyl content of the final alkylbenzene product.

8 Claims, 1 Drawing Sheet

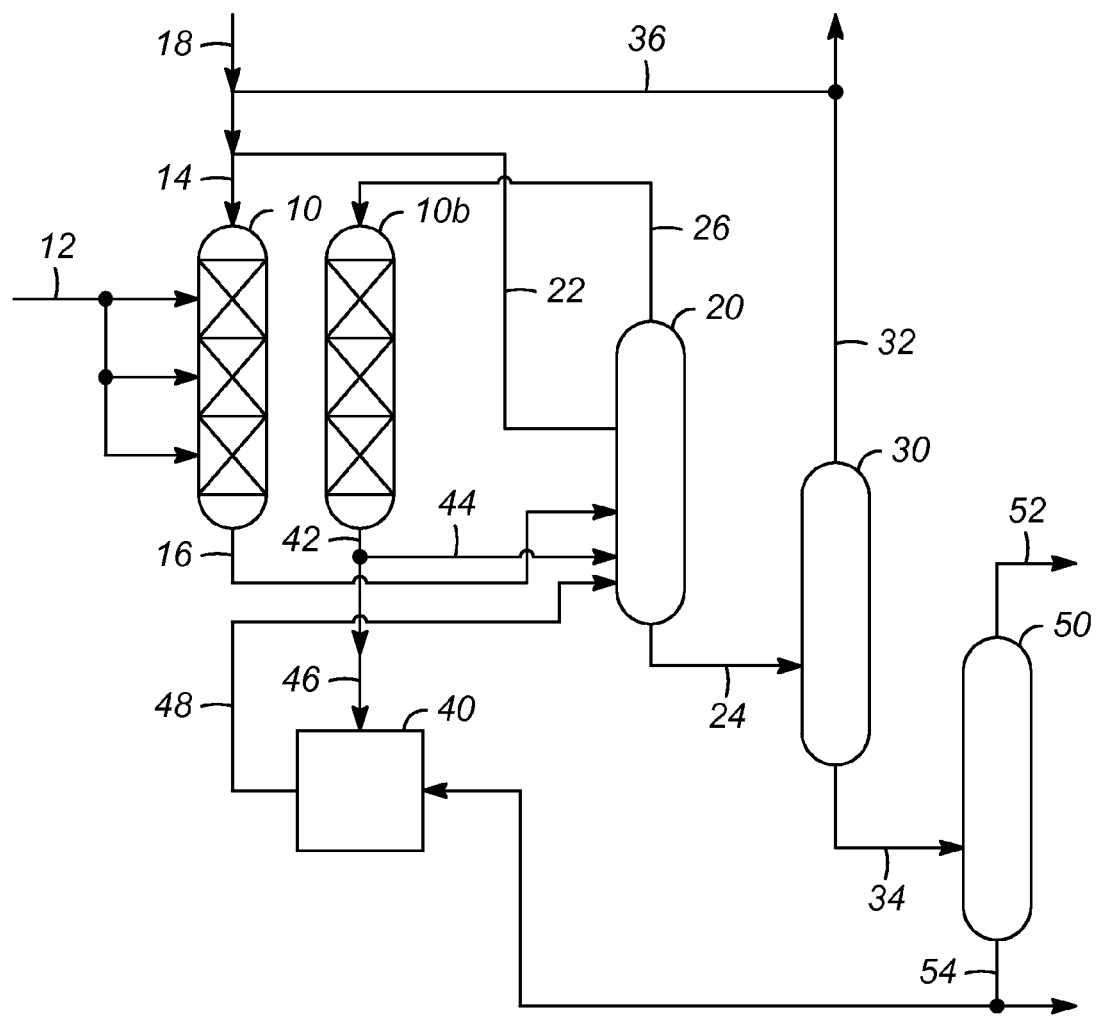

DETERGENT ALKYLATION PROCESS FOR CONTROLLING ALKYLATION EXOTHERM WITH PARAFFINS

FIELD OF THE INVENTION

A process is presented for the production of linear alkylbenzenes. The process includes contacting an aromatic compound with an olefin in the presence of a selective zeolite catalyst. The process further includes the use of an inert compound for moderating the heat release resulting from the reaction.

BACKGROUND OF THE INVENTION

Alkylation of benzene produces alkylbenzenes that may find various commercial uses, e. g., alkylbenzenes can be sulfonated to produce surfactants, for use in detergents. In the alkylation process, benzene is reacted with an olefin of the desired length to produce the sought alkylbenzene. The alkylation conditions comprise the presence of homogeneous or heterogeneous alkylation catalyst such as aluminum chloride, hydrogen fluoride, or zeolitic catalysts and elevated temperature.

Various processes have been proposed to alkylate benzene. One commercial process involves the use of hydrogen fluoride as the alkylation catalyst. The use and handling of hydrogen fluoride does provide operational concerns due to its toxicity, corrosiveness and waste disposal needs. Solid catalytic processes have been developed that obviate the need to use hydrogen fluoride. Improvements in these solid catalytic processes are sought to further enhance their attractiveness through reducing energy costs and improving selectivity of conversion while still providing an alkylbenzene of a quality acceptable for downstream use such as sulfonation to make surfactants.

Alkylbenzenes, to be desirable for making sulfonated surfactants must be capable of providing a sulfonated product of suitable clarity, biodegradability and efficacy. With respect to efficacy, alkylbenzenes having higher 2-phenyl contents are desired as they tend, when sulfonated, to provide surfactants having better solubility and detergency. Thus, alkylbenzenes having a 2-phenyl isomer content in the range from about 30 to about 40 percent are particularly desired. Improvements in the catalysts have facilitated the production of linear alkylbenzenes, as shown in U.S. Pat. No. 6,133,492, U.S. Pat. No. 6,521,804, U.S. Pat. No. 6,977,319, and U.S. Pat. No. 6,756,030. However, the processes can also be further modified to improve the performance of the reaction to obtain better control over the product yields.

SUMMARY OF THE INVENTION

The present invention is a process for the formation of alkylaryl compounds. The process utilizes the inert properties of paraffins for controlling the exotherm during the alkylation process. The process includes passing an aromatic compound to an alkylation zone, and passing a feed stream comprising olefins and paraffins to the alkylation zone. The olefins and aromatic compounds react to form a process stream having alkylaryl compounds. The process stream is then passed to a first fractionation unit to separate the feeds to the fractionation unit into a first bottoms stream having the alkylaryl compounds, and a first fractionation stream having unrected aromatics compounds. The first fractionation stream is passed back to the alkylation zone while the bottoms stream is passed to a second fractionation unit to provide for recycling of the unreacted olefins and some of the paraffins. The bottoms stream from the first fractionation column is passed to a second fractionation unit to generate a second overhead stream having paraffins, and a second bottoms stream having alkylaryl compounds. A portion of the second overhead stream is passed to the alkylation zone.

In a preferred embodiment, the aromatic compound is benzene, and the desired product is a linear alkylbenzene. In the preferred embodiment, the process includes passing the second bottoms stream to a third fractionation zone to generate an overhead stream having a linear alkylbenzene, and a bottoms stream having heavies. The heavies include polyalkylated benzene having dialkylated benzene as the largest fraction. The dialkylated benzene is passed to a transalkylation reaction unit along with benzene to increase the yields of linear alkylbenzenes.

Other objects, advantages and applications of the present invention will become apparent to those skilled in the art from the following detailed description and drawings.

BRIEF DESCRIPTION OF THE DRAWING

FIGURE is a schematic of the present invention.

DETAILED DESCRIPTION OF THE INVENTION

With the use of gas-to-liquid (GTL) technologies for the generation of C9-C16 range material, there is interest from various parties to produce linear alkylbenzenes (LAB) using GTL-based feed source. Current linear alkylbenzene manufacturing process uses kerosene based Pacol-derived C9-C16 material, which is typically a 9-15% mixture of olefins in paraffin. The alkylation of this paraffin/olefin mixture with benzene can be accomplished by solid-bed Detal catalyst. Current state-of-the-art Detal Plus technology using ZDA-2 alkylation catalyst optimizes the solid-bed alkylation technology by maximizing feedstock utilization and minimizing energy consumption. The use of GTL-based paraffin/olefin feedstock to produce commercial grade alkylbenzenes in the C9-C16 range allows to avoid dependence on crude-based feedstock and uses a feedstock that is natural-gas dependent.

In the process scheme, the GTL-based feedstock for alkylation is a mixture of olefins/paraffins. Alkylation of benzene by olefins is an exothermic process, and a higher concentration of olefins in the feed results in a higher exotherm. One method of controlling the exotherm is to recycle additional benzene, as an excess of benzene is used in the alkylation process. However, if only benzene is used, the resulting 2-phenyl content of the final LAB product will be found to be significantly lower than that required for a commercial LAB product.

Both linearity and 2-phenyl are significant properties in the linear alkylbenzene product. Linearity is responsible for the biodegradability of the surfactant, and should be maintained as high as possible, preferably above 90%. The linearity of the LAB is highly dependent on the effluent temperature of the alkylation reactor bed. A higher temperature is detrimental to the linearity and renders the LAB unacceptable for commercial application. 2-phenyl on the other hand determines the solubility and sulfonability of the alkylbenzene, and a precise control of 2-phenyl is required to maintain optimum product quality. 2-phenyl is dependent on the molar ratio of benzene:olefin in the reactor, and a ratio that is higher or lower than the optimum can make the LAB quality unacceptable.

The present process provides for the formation of an alkylaryl compound, while controlling the exotherm. The process, as exemplified by the FIGURE, includes passing a stream 14 comprising an aromatic compound to an alkylation zone 10. A feedstream 12 comprising olefins and paraffins is passed to the alkylation zone 10, wherein the aromatic compound is alkylated over an alkylation catalyst, and a first process stream 16 is generated having alkylaryl compounds. The first process stream 16 is passed to a first fractionation unit 20 to generate a first fractionation stream 22 having unalkylated aromatic compounds. The fractionation unit 20 also generates a first bottoms stream 24 having alkylaryl compounds. The bottoms stream 24 is passed to a second fractionation unit 30 to generate a second overhead stream 32 having paraffins, and a second bottoms stream having alkylaryl compounds 34. The first fractionation stream 22 is returned to the alkylation zone 10. A fresh benzene stream 18 is supplied to make up for benzene consumed in the alkylation process. In one aspect of the process, a portion 36 of the second overhead stream 32 is passed to the alkylation zone 10.

The paraffins present in the process stream provide for moderating the heat rise in the reaction while remaining unreactive in the process. The aromatic compound to be alkylated can include benzene, toluene, ethylbenzene, and xylenes. A preferred aromatic compound is benzene. The alkylation zone 10 comprises one or more alkylation catalyst beds, and can be a fixed catalyst be, or a moving bed system. For the alkylation process with fixed beds, a plurality of beds is desired, such that when one or more beds are on stream, at least one bed can be taken off-line to be regenerated.

In one embodiment, the first fractionation stream 22 is a side draw stream from the rectification section of the first fractionation unit 20. The first fractionation stream 22 can be a low purity aromatics stream generated by the first fractionation unit 20, and can include olefins and paraffins.

The feedstream 12 having olefins and paraffins can be a process stream generated by gas to liquids technology to utilize effluent streams generated from natural gas conversion processes, or from a syngas system, or a Fischer-Tropsch process.

In one embodiment, the process includes generating a high purity aromatics stream 26 from the first fractionation unit 20. The high purity aromatics stream 26 can be passed to an alkylation reactor 10b that is off-line for regeneration of the alkylation catalyst. The aromatics stream passing through the regenerated alkylation unit 10b produces a regeneration effluent stream. The regeneration effluent stream 42 is split into two portions: a first portion 44 and passed to the first fractionation column 20, and a second portion 46 and passed to a transalkylation reactor 40. The second bottoms stream 34 is passed to an LAB column 50 to generate an LAB overhead stream 52 and an LAB bottoms stream 54. A portion of the LAB bottoms stream 54 is passed to the transalkylation reactor 40. The LAB bottoms stream comprises heavies, wherein the heavies are dialkylated aromatic compounds and trialkylated aromatic compounds. The largest fraction of heavies will comprise dialkylbenzenes. The transalkylation reactor 40 will react the benzene, or aromatic compound, from the regenerated alkylation unit 10b with the dialkylbenzene from the heavies stream 54. The transalkylation reactor 40 generates an effluent stream 48 comprising mono-alkylaryl compounds. In particular, the mono-alkylaryl compounds are linear alkylbenzenes. The effluent stream 48 is passed to the first fractionation unit 20 for the recovery of LABs.

In the present process, the feedstream mixture 12 comprises a mixture of olefins and paraffins. The olefin content is in a range from 10 mass % to 30 mass %, and the paraffin content is in the range from 70 mass % to 90 mass %. A preferred mixture of olefins and paraffins in the feedstream includes an olefins content in the range from 20 mass % to 30 mass %, and paraffins in the range from 70 mass % to 80 mass %.

In one embodiment, the process includes splitting the feedstream into at least two portions. The alkylation zone 10 includes two or more alkylation beds. The feedstream is split into a first portion and a second portion. An aromatics stream and the first portion of the feedstream is passed to the first alkylation bed to generate a first alkylation bed effluent stream. The first alkylation bed effluent stream and the second portion of the feedstream is passed to the second alkylation bed to generate a second alkylation bed effluent stream, where the second alkylation bed effluent stream is the first process stream.

This process can include more beds, and a particular example includes a third alkylation bed. The second alkylation effluent stream is passed to the third alkylation bed to generate a third alkylation bed effluent stream, and where the third alkylation bed effluent stream is the first process stream. With the third alkylation bed, an alternative arrangement includes splitting the feedstream into three portions, with the third portion fed to the third alkylation bed.

In another embodiment, the high purity benzene stream can be passed to the transalkylation reactor. The LAB bottoms stream comprising heavies is passed to the transalkylation reactor to generate the transalkylation reactor effluent stream. The transalkylation effluent stream is passed to the benzene column to start the process of separating and recovering the linear alkylbenzenes.

The current process uses a novel process flowscheme to control the product quality of the final LAB product in a detergent alkylation process. The proposed scheme uses a split-bed reactor design that is optimized for feedstock utilization and energy consumption, and adds a feature to this flowscheme to manage the exotherm by increasing the heat-capacity, while still maintaining the desired benzene:olefin ratio in the reactor. If only recycle benzene is used, the resulting 2-phenyl content of the final LAB product will be found to be significantly lower than solid-bed alkylation based commercial grade LAB. Instead of adding more recycle benzene to provide additional heat absorbing capacity, the proposed scheme recycles additional paraffin to lower the exotherm. As the paraffins are unreactive species in the alkylation reactor, the paraffins do not participate in the reaction mechanism. Also, the addition of paraffin allows the maintenance of benzene:olefin ratio in the reactor to obtain optimum product 2-phenyl.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the formation of an alkylaryl compound, comprising:
   passing an aromatic compound to an alkylation zone, wherein the alkylation zone comprises at least two alkylation beds, a first alkylation bed and a second alkylation bed, and the aromatic compound is passed to the first alkylation bed;
   splitting a feedstream comprising olefins and paraffins into at least a first portion and a second portion;
   passing a feedstream the first portion comprising olefins and paraffins to the first alkylation bed, to generate a first intermediate process stream comprising alkylaryl compounds;

passing the first intermediate process stream and the second portion to the second alkylation bed to generate a first process stream;

adding additional paraffins comprising paraffins having a different carbon number and different carbon number range from the olefins to the alkylation zone to bring the paraffin content to at least 70% by weight of the feedstream;

passing the first process stream to first fractionation unit to generate a first fractionation stream comprising a low purity aromatics stream from a side stream from the rectification section of the first fractionation unit, a first bottoms stream comprising alkylaryl compounds; and an overhead stream comprising high purity aromatics stream;

passing the bottoms stream to a second fractionation unit to generate a second overhead comprising paraffins, and a second bottoms stream comprising alkylaryl compounds;

passing the first fractionation stream to the alkylation zone;

passing a portion of the second overhead stream to the alkylation zone;

passing the high purity aromatics stream to an alkylation reactor in regeneration mode, thereby creating a regeneration effluent stream;

splitting the regeneration effluent stream into a first portion and a second portion;

passing the first portion to the first fractionation column;

passing the second portion to a transalkylation reactor;

passing the second bottoms stream from the second fractionation column to an LAB column to generate an LAB overhead stream comprising LABs, and an LAB bottoms stream comprising heavies;

passing a portion of the LAB bottoms stream to the transalkylation reactor to create a transalkylation effluent stream comprising mono-alkylaromatic compounds; and passing the transalkylation effluent stream to the first fractionation unit.

2. The process of claim 1 wherein the aromatic compound is benzene.

3. The process of claim 1 wherein the alkylation zone comprises a fixed catalyst bed comprising an alkylation catalyst.

4. The process of claim 1 wherein the feedstream comprises an effluent from a gas to liquids technology.

5. The process of claim 4 wherein the feedstream comprises an effluent from a syngas system or a Fischer-Tropsch system.

6. The process of claim 1 wherein the feedstream mixture comprises olefins in the range from 10 mass % to 30 mass % and paraffins in the range from 70 mass % to 90 mass %.

7. The process of claim 6 wherein the feedstream mixture comprises olefins in the range from 20 mass % to 30 mass % and paraffins in the range from 70 mass % to 80 mass %.

8. The process of claim 1 further comprising a third alkylation bed, wherein the effluent stream from the second alkylation bed is passed to the third alkylation bed, and wherein the effluent from the third alkylation bed is the first process stream.

* * * * *